(12) United States Patent
MacLaughlin et al.

(10) Patent No.: US 6,692,738 B2
(45) Date of Patent: Feb. 17, 2004

(54) DELIVERY OF THERAPEUTIC BIOLOGICALS FROM IMPLANTABLE TISSUE MATRICES

(75) Inventors: David T. MacLaughlin, Saugus, MA (US); Joseph P. Vacanti, Winchester, MA (US); Patricia K. Donahoe, Boston, MA (US); Peter T. Masiakos, Boston, MA (US)

(73) Assignee: The General Hospital Corporation, Boston, MA (US)

(*) Notice: Subject to any disclaimer, the term of this patent is extended or adjusted under 35 U.S.C. 154(b) by 155 days.

(21) Appl. No.: 09/770,339

(22) Filed: Jan. 26, 2001

(65) Prior Publication Data

US 2002/0031500 A1 Mar. 14, 2002

Related U.S. Application Data

(60) Provisional application No. 60/178,842, filed on Jan. 27, 2000.

(51) Int. Cl.[7] .......................... A61K 48/00; A61K 9/14; C12N 5/00; C12N 15/63
(52) U.S. Cl. ..................... 424/93.21; 424/484; 435/455; 435/325
(58) Field of Search .............................. 424/93.21, 486, 424/484, 497; 514/44; 435/325, 320.1, 455

(56) References Cited

U.S. PATENT DOCUMENTS

| | | |
|---|---|---|
| 4,404,199 A | 9/1983 | Bonaldi et al. |
| 4,487,833 A | 12/1984 | Donahoe et al. |
| 4,510,131 A | 4/1985 | Donahoe et al. |
| 4,753,794 A | 6/1988 | Donahoe |
| 4,792,601 A | 12/1988 | Donahoe et al. |
| 5,011,687 A | 4/1991 | Donahoe et al. |
| 5,047,336 A | 9/1991 | Cate et al. |
| 5,198,420 A | 3/1993 | Donahoe et al. |
| 5,204,055 A | 4/1993 | Sachs et al. |
| 5,661,126 A | 8/1997 | Donahoe et al. |
| 5,709,854 A | 1/1998 | Griffith-Cima et al. |
| 5,759,830 A | 6/1998 | Vacanti et al. |

FOREIGN PATENT DOCUMENTS

| | | |
|---|---|---|
| WO | WO 93/17669 | 9/1993 |
| WO | WO 94/00133 | 1/1994 |
| WO | WO 94/25080 | 11/1994 |
| WO | WO 96/40002 | 12/1996 |

OTHER PUBLICATIONS

Amalfitano and Parks, "Separating Fact from Fiction: Assessing the Potential of Modified Adenovirus Vectors for Use in Human Gene Therapy", Current Gene Therapy, 2002, 2, 111–133.
Li and Ma, "Nonviral Gene Therapy" Current Gene Therapy, 2001, 1, 201–226.
Gilbert et al., "Cell transporation of genetically altered cells on biodegradable polymer scaffolds in syngeneic rats" Transplantation, vol. 56, Aug. 2, 1998, pp. 423–427.
Qin et al., "Interferon–beta gene therapy inhibits tumor formation and causes regression of established tumors in immune–deficient mice" Proc. Natl. Acad. Sci. USA, vol. 95, Nov. 1998, pp. 14411–14416.
Cao et al., "Expression of angiostatin cDNA in a murine fibrosarcoma supresses primary tumor growth and produces long–term dormancy of metastases" J. Clin. Invest., vol. 101, No. 5, Mar. 5, 1998, pp. 1055–1063.
Vacanti & Langer, "Tissue engineering: the designs and fabrication of living replacement devices for surgical reconstruction and transplantation" The Lancet, vol. 34, No. Suppl.Jul. 24, 1999, pp. 32–34.

(List continued on next page.)

Primary Examiner—Ram R. Shukla
(74) Attorney, Agent, or Firm—Frommer Lawrence Haug LLP; Thomas J. Kowalski; Amy Lesby

(57) ABSTRACT

Normal cells, such as fibroblasts or other tissue or organ cell types, are genetically engineered to express biologically active, therapeutic agents, such as proteins that are normally produced in small amounts, for example, MIS, or other members of the TGF-beta family Herceptin™, interferons, andanti-angiogenic factors. These cells are seeded into a matrix for implantation into the patient to be treated. Cells may also be engineered to include a lethal gene, so that implanted cells can be destroyed once treatment is completed. Cells can be implanted in a variety of different matrices. In a preferred embodiment, these matrices are implantable and biodegradable over a period of time equal to or less than the expected period of treatment, when cells engraft to form a functional tissue producing the desired biologically active agent. Implantation may be ectopic or in some cases orthotopic. Representative cell types include tissue specific cells, progenitor cells, and stem cells. Matrices can be formed of synthetic or natural materials, by chemical coupling at the time of implantation, using standard techniques for formation of fibrous matrices from polymeric fibers, and using micromachining or microfabrication techniques. These devices and strategies are used as delivery systems via standard or minimally invasive implantation techniques for any number of parenterally deliverable recombinant proteins, particularly those that are difficult to produce in large amounts and/or active forms using conventional methods of purification, for the treatment of a variety of conditions that produce abnormal growth, including treatment of malignant and benign neoplasias, vascular malformations (hemangiomas), inflammatory conditions, keloid formation, abdominal or plural adhesions, endometriosis, congenital or endocrine abnormalities, and other conditions that can produce abnormal growth such as infection. Efficacy of treatment with the therapeutic biologicals is detected by determining specific criteria, for example, cessation of cell proliferation, regression of abnormal tissue, or cell death, or expression of genes or proteins reflecting the above.

8 Claims, 3 Drawing Sheets

OTHER PUBLICATIONS

Stephen et al., "Tissue–engineered cells producing complex recombinant proteins inhibit ovarian cancer in vivo" Proc. Natl. Acad. Sci. USA, vol. 98, No. 6, Mar. 13, 2001, pp. 3214–3219.

Segev et al. (2001) "Mullerian Inhibiting Substance Regulates NFkB Signalling and Growth of Mammary Epithelial Cells in Vitro" Journal of Biological Chemistry, vol. 276(29), Issue of Jul. 20, pp. 26799–26806.

Stephen et al. (2002) "Highly Purified Mullerian Inhibiting Substance Inhibits Human Ovarian cancer in Vivo" Clinical Cancer Research, vol. 8, pp. 2640–2646.

Lorenzo et al. (2002) "New Approaches for High–Yield Purification of Mullerian Inhibiting Substance Improve Its Bioactivity" Journal of Chromatography B: Analytical Technologies in the Biomedical and Life Sciences, vol. 766, Issue 1, pp. 89–98.

Segev et al. (2002)"Mullerian–inhibiting substance regulates NF–kB signalling in the prostate in vitro and in vivo" PNAS, vol. 99(1), pp. 239–244.

Segev et al. (2000) "Mullerian Inhibiting Substance Inhibits Breast Cancer Cell Growth through an NFkB–mediated Pathway" Journal of Biological Chemistry, vol. 275(37), Issue of Sep. 15, pp. 28371–28379.

Bogden, et al., "Growth of human tumor xenografts implanted under the renal of normal immunocompetent mice," *Exp Cell Biol* 47(4):281–93 (1979).

Boveri, et al., "Transfection of the Mullerian inhibiting substance gene inhibits local and metastatic tumor growth," *Int J Oncology* 2:135–44 (1993).

Budzik, et. al., "Mullerian inhibiting substance fractionation by dye affinity chromatography," *Cell* 34:307–314 (1983).

Cate, et al., Isolation of the bovine and human genes for Mullerian inhibiting substance and expression of the human gene in animal cells, *Cell* 45:685–98 (1986).

Cate, et. al., "Development of Mullerian inhibiting substance as an anti–cancer drug," *Cold Spring Harbor Symp Quant Biol* 51(Pt 1):641–7 (1986).

Chamberlain, et al., "Early peripheral nerve healing in collagen and silicone tube implants: myofibroblasts and the cellular response," *Biomaterials* 19(15):1393–1403 (1998).

Chin, et al., "Human mullerian inhibiting substance inhibits tumor growth in vitro and in vivo," *Cancer Research* 51:2101–2106 (1991).

Donahoe, et al., "A graded organ culture assay for the detection of Mullerian inhibiting substance," *J Surg Res* 23: 141–8 (1977).

Donahoe, et al., "Mullerian duct regression in the embryo correlated with cytotoxic activity against human ovarian cancer," *Science* 205:913–5 (1979).

Donahoe, et al., "Mullerian inhibiting substance inhibits growth of a human ovarian cancer in nude mice," *Ann Surgery* 194:472–80 (1981).

Fingert, et al., "Rapid growth of human cancer cells in a mouse model with fibrin clot subrenal capsule assay," *Cancer Res.* 47:3824–3829 (1987).

Fuller, et al., "Mullerian inhibiting substance inhibits colony growth of a human ovarian carcinoma cell line," *J Clin Endocr Metab.* 54:1051–5 (1982).

Fuller, et al., "Mullerian inhibiting substance reduction of colony growth of human gynecologic cancers in a stem cell assay," *Gynecol Oncol.* 22:135–148 (1985).

Gustafson, et al, "Mullerian inhibiting substance as a marker for ovarian sex–cord tumor," *N. Eng. J. Med.* 326(7):466–471 (1992).

Hadlock, et al., "A novel, biodegradable polymer conduit delivers neurotrophins and promotes nerve regeneration," *Laryngoscope* 109(9):1412–1416 (1999).

Hudson, et al., "An immunoassay to detect human mullerian inhibiting substance in males and females during normal development," *J Clin Endocrinol Metab.* 70:16–22 (1990).

Kristjansen, et al., "Tissue–isolated human tumor xenografts in athymic nude mice," *Microvasc. Res.* 48:389–402 (1994).

Kurian, et al., "Cleavage of Mullerian inhibiting substance activates antiproliferative effects in vivo," *Clin. Cancr Res.* 1(3):343–349 (1995).

Lee, et al., "Mullerian inhibiting substances in humans: normal levels from infancy to adulthood," *J Clin Endocrinol Metab.* 81:571–69 (1996).

Maclaughlin, et al., "Bioassay, purification, cloning, and expression of Mullerian inhibiting substance," *Methods Enzymol.* 198:358–69 (1991).

MacLaughlin, et al., "Mullerian duct regression and antiproliferative bioactivities of mullerian inhibiting substance reside in its carboxy–terminal domain," *Endocrinology* 131(1):291–6 (1992).

Masiakos, et al., "Human ovarian cancer, cell lines, and primary ascites cells express the human Mullerian inhibiting substance (MIS) type II receptor, bind, and are responsive to MIS," *Clinical Cancer Research* 5(11):3488–99 (1999).

Matsuda, et al., "Photoinduced prevention of tissue adhesion," *ASAIO Trans.* 38:154–157 (1992).

O'Reilly, et al., "Antiangiogenic activity of the cleaved conformation of the serpin antithrombin," *Science* 285(5435):1926–8 (1999).

Parry, et al., "Recombinant human mullerian inhibiting substance inhibits human ocular melanoma cell lines in vitro and in vivo," *Cancer Res.* 52:1182–6 (1992).

Pepinsky, et al., "Proteolytic processing of mullerian inhibiting substance produces a transforming growth factor–beta–like fragment," *J. Biol. Chem.* 263:18961–41 (988).

Ragin, et al., "Human mullerian inhibiting substance: enhanced purification imparts biochemical stability and restores antiproliferative effects," *Protein Expression and Purification* 3(3):236–45 (1992).

Teixeira, et al., "Developmental expression of a candidate mullerian inhibiting substance type II receptor," *Endocrinology* 137(1):160–5 (1996).

Teixeria, et al., "Transcriptional regulation of the rat Mullerian inhibiting substance type II receptor in rodent Leydig cells," *PNAS* (1999).

Wells, et al., "Gel matrix vehicles for growth factor application in nerve gap injuries repaired with tubes: a comparison of biomatrix, collagen, and methylcellulose," *Exp. Neurol.* 146(2):395–402 (1997).

Woerly, et al., "Neural tissue formation within porous hydrogels implanted in brain and spinal cord lesions: ultrastructural, immunohistochemical, and diffusion studies," *J. Tissue Engineering* 5(5):467–488 (1999).

DELIVERY OF THERAPEUTIC BIOLOGICALS FROM IMPLANTABLE TISSUE MATRICES

This application claims priority to U.S. Ser. No. 60/178,842 filed Jan. 27, 2000.

The United States government has certain rights in this invention by virtue of Grant No. CA17393 from the National Institutes of Health to Patricia K. Donahoe and David T. MacLaughlin; National Institute of Health grant No. CA71345; and Department of Defense 1200-202487 to Joseph P. Vacanti.

BACKGROUND OF THE INVENTION

The present invention is generally in the area of methods and systems for treatment of disorders such as cancer with biologically active agents produced naturally by cells in extremely small quantities, using genetically engineered host cells or natural cells that secrete a substance naturally implanted in biodegradable polymeric matrices.

One of the difficulties in treatment of conditions such as cancer using protein or other biological modifiers is the need for large quantities of the therapeutic agent to be delivered over an extended period of time. For most of the compounds discovered during research on complex pathways or unique tissues, it has not been possible, or has not been commercially feasible, to produce the compounds in sufficient quantity to treat the disorders. Numerous examples of these compounds, especially proteins, have been reported. One prominent example is angiostatin, a naturally occurring anti-angiogenic peptide identified by researchers at Children's Medical Center in Boston, Mass. Although extremely promising in mice (O'Reilly et al., Science 285(5435):1926–8 1999), the inability of the developers to produce large quantities of the peptide has proven to be a major stumbling block to conducting clinical trials for treatment of cancer.

Mullerian Inhibiting Substance (MIS) is another biological with great potential for treatment of cancer. MIS is produced by the fetal testis and causes the regression in males of the Müllerian duct, the forerunner of the female reproductive ducts. MIS has been shown to have great potential as a treatment for ovarian carcinomas (Chin et al, Cancer Research. 51:2101–2106, 1991; Masiakos, et al, Clinical Cancer Research, 5(11):3488–99 1999) which are derived from embryonic Müllerian structures. Recombinant human MIS (rhMIS) produced in Chinese hamster ovary cells (CHO) in multiple roller bottles has antiproliferative activity against several human carcinoma cell lines (Chin, et al, 1991). Recently, it was also reported that rhMIS specifically binds to a functional heteromeric serine threonine (Teixeira, et al., Androl. 17(4):336–41 1996; Teixeira et al., Endocrinology Jan;137(1):160–5 1996) receptor on the surface of human ovarian cancer ascites cells and inhibits the growth in vitro of these cells and of cells obtained directly from women with Stage III and IV disease (Masiakos et al., 1999). See also, U.S. Pat. Nos. 4,404,199, 4,487,833, 4,510,131, 4,753,794, 4,792,601, 5,011,687, 5,198,420 and 5,661,126 to Donahoe, et al., the teachings of which are incorporated by reference herein.

The Pediatric Surgical Research Laboratories has tested the hypothesis that MIS will be a useful therapeutic agent for certain epithelial ovarian cancers in a number of in vitro studies described below, but only limited trials have been conducted in vivo. A major obstacle has been purifying sufficient recombinant protein of suitable potency and homogeneity for patient use.

Late stage epithelial ovarian cancer is a common and highly lethal gynecologic malignancy. Despite advances in treatment over the past two decades substantial improvement in overall survival has been slow and incremental and a high mortality remains. The coelomic epithelium, which invaginates to form the Müllerian duct, is also the origin of these highly lethal human ovarian cancers. The hypothesis that MIS is a therapeutic for these Müllerian derived tumors is predicated on previous observations in which partially purified bovine MIS (Donahoe et al., J Surg Res. 23: 141–8, 1977) suppressed growth of a single human ovarian cancer cell line in monolayer culture (Donahoe et al., Science. 205:913–5, 1979), in stem cell assays (Fuller et al., J Clin Endocr Metab. 54:1051–5, 1982), and in vivo in nude mice (Donahoe et al., Ann Surgery. 194:472–80,1981). Additionally, bovine MIS inhibited the growth of a large number of primary ovarian, Fallopian, and uterine carcinomas obtained directly from patients and tested in colony inhibition assays in soft agar (Fuller et al., Gynecol. Oncol. 22:135–148, 1985). After purifying bovine MIS (Budzik et. al., Cell 34: 307–314, 1983), the bovine and human MIS cDNAs and genomic human MIS (Cate et al., Cell. 45: 685–98 1986) were cloned. The human gene was used to produce highly purified recombinant human MIS (rhMIS) (Cate et. al., Cold Spring Harbor Symp Quant Biol 51 Pt 1:641–7 1986; MacLaughlin et al., Methods Enzymol. 198: 358–69, 1991) to which monoclonal and polyclonal antibodies were raised for use in a sensitive ELISA (Hudson et al., J Clin Endocrinol Metab. 70: 16–22, 1990; Lee et al J Clin Endocrinol Metab. 81:571–69, 1996). The rhMIS, which is now produced in a series of roller bottles and purified from the media (Ragin et al, Protein Expression and Purification, 1992; 3(3):236–45), was shown to inhibit three human carcinoma cell lines of Müllerian origin (Chin et al., 1991), as well as a human ocular melanoma cell line (Parry et al., Cancer Res. 52:1182–6, 1992), in vitro and in vivo, in a dose dependent manner (Chin et al., 1991; Boveri et al., Int J Oncology. 2; 135–44, 1993). In order to scale up production beyond the roller bottle capacity which suites academic needs, a clonal line of MIS-producing transfected CHO cells (CHO, B9) was transferred to CHO B9 seeded bioreactors, for scale up to complete the phase I trials. Purification protocols for the bioreactor produced protein have been designed (Ragin et al, 1992), but modifications to improve purification protocols to enhance recovery and cioactivity have not resulted in production of sufficient quantities.

It is important to note that like the other members of the TGFβ family, the bioactive purified protein is not a single polypeptide chain but a proteolytically cleaved molecule. MIS is primarily processed at residue 427, producing 110 kDa amino-terminal and 25 kDa carboxyterminal disulfide bond reduction sensitive homodimers (Pepinsky et al, J. Biol. Chem. 1988; 263:18961–4.; MacLaughlin et al, Endocrinology Jul;131(1):291–6 1992). Although the carboxy terminus is the active domain of rhMIS in vitro, it has not been shown to be active in vivo. The non-covalent association of the amino and carboxy termini is presumed to prevent the rapid clearance characteristic of the C terminus in vivo. Therefore, MIS to be administered to patients is being produced as a cleaved but non-dissociated complex. Unfortunately, the immunoaffinity purification protocols result in aggregation, given the hydrophobic character of MIS, with a product of reduced potency and low yield, making a process consistent with general manufacturing practices problematic. Moreover, alternative systems which are more efficient for large scale in vitro production, such as bacterial, yeast, or insect cell expression systems, have not been successful for the production of biologically active preparations of MIS.

It is therefore an object of the present invention to provide methods and reagents for production of clinically effective amounts of therapeutic biologicals, especially proteins such as MIS, in vivo.

It is a further object of the present invention to provide methods and reagents for production of biologics in vivo, where the production can be discontinued if appropriate.

It is a still further object of the present invention to provide methods and reagents for treatment of a variety of disorders characterized by the proliferation of abnormal tissue, including malignant and benign neoplasias, vascular malformations, inflammatory conditions including restenosis, infection, keloid formation and adhesions, congenital or endocrine abnormalities and other conditions that produce abnormal growth.

SUMMARY OF THE DISCLOSURE

Normal cells, such as fibroblasts or other tissue or organ cell types, are genetically engineered to express biologically active, therapeutic agents, such as proteins that are normally produced in small amounts, for example, MIS, Herceptin™, interferons, and Endostatin™, or naturally produced compounds. These cells are seeded into a matrix for implantation into the patient to be treated. Cells may also be engineered to include a lethal gene, so that implanted cells can be destroyed once treatment is completed. Cells can be implanted in a variety of different matrices. In a preferred embodiment, these matrices are implantable and biodegradable over a period of time equal to or less than the expected period of treatment, during which the engrafted cells form a functional tissue producing the desired biologically active agent for longer periods of time. Representative cell types include tissue specific cells, progenitor cells, and stem cells. Matrices can be formed of synthetic or natural materials, by chemical coupling at the time of implantation, using standard techniques for formation of fibrous matrices from polymeric fibers, and using micromachining or microfabrication techniques.

These devices and strategies are used as delivery systems, which may be implanted by standard or minimally invasive implantation techniques, for any number of parenterally deliverable recombinant proteins, particularly those that are difficult to produce in large amounts and/or active forms using conventional methods of purification, for the treatment of a variety of conditions that produce abnormal growth, including treatment of malignant and benign neoplasias, vascular malformations (hemangiomas), inflammatory conditions, keloid formation and adhesion, endometriosis, congenital or endocrine abnormalities, and other conditions that can produce abnormal growth such as infection. Efficacy of treatment with the therapeutic biologicals is detected by determining specific criteria, for example, cessation of cell proliferation, regression of abnormal tissue, or cell death.

The examples demonstrate the use of this method with a tissue specific biological modifier, MIS. Genetically engineered CHO cells were grown on implantable polymeric meshes and the levels of secreted rMIS measured. The polymeric meshes with CHO cells seeded therein were then implanted in vivo and serum levels of rMIS measured. Data show very high levels of rMIS over prolonged time periods. These animals were then implanted with human ovarian cell lines and tumor regression measured in the presence of the MIS-producing cells. The implanted cells significantly inhibited the tumor cell proliferation.

BRIEF DESCRIPTION OF THE DRAWINGS

FIG. 2A is a graph showing that the accumulation of MIS in serum is influenced by the size of the polymer implant. Polymer squares were seeded with MIS-producing CHO-B9 cells 3 days prior to implantation. After 21 days, marked differences in the mean serum levels of MIS (n=4 per polymer size) can be seen in the animals implanted with polymers of varying sizes. 0.5 $cm^2$ grafts were used for further study.

FIG. 2B is a graph showing increasing levels of MIS were detected by ELISA on day 7, 14, 21, and 28 in the serum of SCID mice after the CHO-B9 seeded polymer was implanted in the right ovarian pedicle. This composite figure shows the mean +/− the standard error of the mean for a total of 40 animals.

FIG. 2C is a graph showing that the accumulation of MIS in the serum of polymer-bearing mice is reversible. Two weeks after implantation of a polymer-cell graft into the right ovarian pedicle of a SCID mouse the serum level of MIS was approximately 1200 ng/ml. Upon removal of the polymer, the MIS falls to undetectable levels, consistent with lack of migration of MIS-producing cells from the site of implantation (n=1).

FIG. 3A shows that the mean graft-size ratios (GSR) +/− the standard error of the mean of the IGROV-1 tumors in the animals producing bioactive MIS (n=8) was significantly smaller than the IGROV-1 tumors exposed to bioinactive MIS (n=10) (p value=0.016). A GSR of 1 indicates no net growth.

FIG. 3B shows that the mean GSR of the IGROV-1 tumors implanted in the animals with MIS-producing CHO-B9 polymer (n=30) was significantly smaller than the IGROV-1 tumors implanted in the animals with empty polymer (n=30) (p value<0.001).

DETAILED DESCRIPTION OF THE INVENTION

Figure 1:
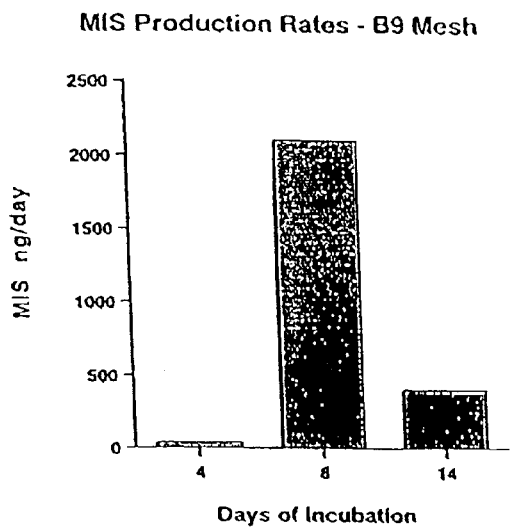
FIG. 1 is a graph of MIS (ng/day) production over days of incubation of CHO B9 cells impregnated on mesh in vitro.

A strength of biological modifiers is that they impart specificity to treatment paradigms to allow for prolonged parenteral therapy, and eliminate many of the side effects and inconveniences associated with conventional therapies. Problems which are often encountered with these molecules include purification and enrichment. Most are manufactured in the laboratory using recombinant technology. A small number are selected for scale up by the pharmaceutical industry. As an important step for their purification, they undergo rigorous purification schemes using separation methods that may alter their chemical characteristics. As is often the case, the end product is a small percentage of the starting material, and is frequently less potent. To obviate the loss of quantity and potency, a polymer scaffolding or matrix has been used to proliferate cells producing the biological modifiers. When this scaffold or matrix is implanted into an organism, it becomes vascularized or otherwise connected to the vasculature, the seeded cells grow to fill the scaffold, the biological modifiers are secreted directly into the bloodstream or adjacent cells, and, in a preferred embodiment, the scaffold is resorbed, leaving a new secretory tissue. Elimination of the purification steps enhances yield and avoids the problems with contamination, cost and loss of biological activity.

I. Materials for Production of Secretory Tissues

The materials required for production in vivo of biologically active molecules include cells which produce the biologically active molecules and matrices for proliferation of the engineered cells which can be implanted in vivo to form new secretory tissues. In one embodiment, cells are obtained which already produce the desired biological modifiers. In another embodiment, cells are genetically engineered to produce the biological modifiers. In this embodiment, it is also necessary to provide the appropriate genes, means for transfection of the cells, and means for expression of the genes.

A. Cells to be Engineered

As a proof of principle, CHO cells permanently transfected by calcium phosphate precipitation with the MIS gene on a CMV promotor and clonally selected for the highest MIS producers were used in preparations and implantations. The devices were seeded with cells for 4–7 days prior to implantation and MIS levels measured in the serum by a sensitive MIS ELISA. The next step was to implant nontumor cells, such as fibroblasts, both cell lines and then the patient's own fibroblasts to avoid rejection. These cells likewise can be engineered to express, and secrete the desired biological molecule(s). Other representative cell types include other patient specific differentiated cells, progenitor or embryonic or pluripotential stem cells.

Cells to be engineered can be obtained from established cell culture lines, by biopsy or from the patient or other individuals of compatible tissue types. The preferred cells are those obtained from the patient to be treated. In those cases where the patient's own cells are not used, the patient will also be treated with appropriate immunosuppressants such as cyclosporine to avoid destruction of the implanted cells during therapy.

In the preferred embodiments, cells are obtained directly from the donor, washed, and cultured using techniques known to those skilled in the art of tissue culture. Cells are then transfected with the gene of interest and seeded at various cell counts onto a matrix such as a polymeric mesh to achieve optimal production of a biological such as MIS.

Cell attachment and viability can be assessed using scanning electron microscopy, histology, and quantitative assessment, for example, by ELISA, fluorescent labelled or radioactive labelled antibodies. The function of the implanted cells can be determined using a combination of the above-techniques and functional assays. Studies using protein assays can be performed to quantitate cell mass on the polymer scaffolds. These studies of cell mass can then be correlated with cell functional studies to determine the appropriate cell mass.

B. Biologically Active Molecules

Any biologically active molecule which has been cloned or for which a cellular source is available can be used. Representative molecules are those having a known activity which selectively reduces the symptoms of the disorder to be treated, such as MIS, Herceptin, interferons, endostatin, and growth factors such as tumor necrosis factor. For example, for the treatment of malignant or benign hyperplasia, the biologically active molecules include anti-angiogenic compounds, MIS and other hormones which selectively or preferentially bind to the cells to be killed or inactivated. Alternatively, the cells can be engineered to correct the defect in the cells which results in overproliferation.

The goal is not to form a permanent new tissue, but to provide an implanted "bioreactor" to produce therapeutic biologicals for a defined period effective to cause cessation of cell proliferation, regression of abnormal tissue, or cell death. Various devices and strategies are used as delivery systems which can be transplanted by standard or by minimally invasive implantation techniques for any number of parenterally deliverable recombinant proteins, particularly those that are difficult to produce in large amounts and/or active forms using conventional methods of purification, for the treatment of a variety of conditions that produce abnormal growth, including treatment of malignant and benign neoplasias, vascular malformations (hemangiomas), inflammatory conditions, keloid formation, endometriosis, congenital or endocrine abnormalities, and other conditions that can produce abnormal growth such as infection.

C. Vectors for Engineering Cells

Examples of recombinant DNA techniques include cloning, mutagenesis, and transformation. Recombinant DNA techniques are disclosed in Maniatis et al., Molecular Cloning: A Laboratory Manual, Cold Spring Harbor, N.Y. (1982). Vectors, including adeno-associated viruses, adenoviruses, retroviruses, and tissue specific vectors, are commercially available. Vectors can include secretory sequences, so that the biological modifier will diffuse out of the cell in which it is expressed and into the vascular supply or interstitial spaces in order to expose the cells of interest to concentrations of the protein that are effective to treat the patient. The vector or expression vehicle, and in particular the sites chosen therein for insertion of the selected DNA fragment and the expression control sequence, are determined by a variety of factors, e.g., number of sites susceptible to cleavage by a particular restriction enzyme, size of the protein to be expressed, expression characteristics such as start and stop codons relative to the vector sequences, and other factors recognized by those of skill in the art. The choice of a vector, expression control sequence, and insertion site for DNA sequence encoding the biological modifier is determined by a balance of these factors.

It should be understood that the DNA sequences coding for the biological modifier that are inserted at the selected site of a cloning or expression vehicle may include nucleotides which are not part of the actual gene coding for the biological modifier or may include only a fragment of the actual gene. It is only required that whatever DNA sequence is employed, a transformed host cell will produce the biological modifier. For example, MIS DNA sequences may be fused in the same reading frame in an expression vector with at least a portion of a DNA sequence coding for at least one eukaryotic or prokaryotic signal sequence, or combinations thereof. Such constructions enable the production of, for example, a methionyl or other peptidyl-MIS polypeptide. This N-terminal methionine or peptide may either then be cleaved intra- or extra-cellularly by a variety of known processes or the MIS polypeptide with the methionine or peptide attached may be used, uncleaved.

The complete nucleotide and amino acid sequence for human and bovine MIS, and cloning and expression vehicles, are provided in U.S. Pat. No. 5,047,336 to Cate, et al. and Cate et al., Cell 45:685–698(1986), and are also available using publicly available gene data bases and commercial suppliers.

D. Matrices

There are three basic types of matrices that can be used: devices formed by micromachining, micromolding or other microfabrication techniques, fibrous polymeric scaffolds, and hydrogels.

1. Microfabricated Device Design and Manufacture

Preferred materials for making devices to be seeded with cells are biodegradable polymers, although in some embodiments non-degradable materials may be preferred or may be used as structural support or as components of a device formed of biodegradable polymer. The polymer composition can be selected both to determine the rate of degradation as well as to optimize proliferation. Many biodegradable, biocompatible polymeric materials can be used to form the device, or guide channels within the device, including both natural and synthetic polymers, and combinations thereof. Examples of natural polymers include proteins such as collagen, collagen-glycosaminoglycan copolymers, polysaccharides such as the celluloses (including derivatized celluloses such as methylcelluloses), extracellular basement membrane matrices such as Biomatrix, and polyhydroxyalkanoates such as polyhydroxybutyrate (PHB) and polyhydroxybutyrate-co-valerate (PHBV) which are produced by bacterial fermentation processes. Synthetic polymers include polyesters such as polyhydroxyacids like polylactic acid (PLA), polyglycolic acid (PGA) and compolymers thereof (PLGA), some polyamides and poly(meth)acrylates, and polyanhdyrides. Examples of non-degradable polymers include ethylenevinylacetate (EVA), polycarbonates, and some polyamides.

The surface morphology of the devices can affect cell growth. Bioactive materials may also be incorporated into the device or a sustained release matrix within the device to promote cell viability or proliferation. These materials can be incorporated into the polymer at a loading designed to release by diffusion and/or degradation of the polymer forming the device over a desired time period, ranging from days to weeks. Alternatively, the bioactive substance may be incorporated into a matrix loaded into or adjacent to the device. These matrices may be formed of the same materials as the device or may consist of polymeric materials incorporated within the tracts or channels, for example, hydrogel matrices of the types described in the literature (for example, Wells, et al., Exp. Neurol. (1997) 146(2):395–402; Chamberlain, et al., Biomaterials 1998 19(15):1393–1403; and Woerly, et al., (1999) J. Tissue Engineering 5(5):467–488) for use in promoting nerve growth. Examples of such materials include polyamide, methylcellulose, polyethyleneoxide block compolymers such as the Pluronics, especially F127 (BASF), collagen, and extracellular matrix (ECM) of the type sold as Biomatrix. Other useful materials include the polymer foams reported by Hadlock, et al., Laryngoscope (1999) 109(9):1412–1416.

Microfabrication techniques include micromachining, solid free form (SFF) techniques, and micromolding techniques, as well as other techniques based on well-established methods used to make integrated circuits, electronic packages and other microelectronic devices, having dimensions as small as a few nanometers and which can be mass produced at low per-unit costs.

Micromachining Techniques

Micromachining techniques are described in the literature, for example, by Rai-Choudhury, ed. Handbook of Microlithography, Micromaching & Microfabrication (SPIE Optical Engineering Press, Bellingham, Wash. 1997), the teachings of which are incorporated herein. The techniques can be used to form the device directly, or as discussed below, to form molds which are then used to form the devices.

Other microfabrication processes that may be used include lithography; etching techniques, such as wet chemical, dry, and photoresist removal; thermal oxidation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, laser machining, and laser ablation (including projection ablation). See generally Jaeger, *Introduction to Microelectronic Fabrication* (Addison-Wesley Publishing Co., Reading Mass. 1988); Runyan, et al., Semiconductor Integrated Circuit Processing Technology (Addison-Wesley Publishing Co., Reading Mass. 1990); *Proceedings of the IEEE Micro Electro Mechanical Systems Conference* 1987–1998; Rai-Choudhury, ed., *Handbook of Microlithograhy Micromachining & Microfabrication* (SPIE Optical Engineering Press, Bellingham, Wash. 1997).

Deep plasma etching can be used to create structures with diameters on the order of 0.1 $\mu$m or larger. In this process, an appropriate masking material is deposited onto a substrate and patterned into dots having the diameter of the desired tracts or channels. The wafer is then subjected to a carefully controlled plasma. Those regions protected by the metal mask remain and form the tracts.

Another method for forming devices including tracts or channels is to use microfabrication techniques such as photolithography, plasma etching, or laser ablation to make a mold form, transferring that mold form to other materials using standard mold transfer techniques, such as embossing or injection molding, and reproducing the shape of the original mold form using the newly-created mold to yield the final device. Alternatively, the creation of the mold form could be skipped and the mold could be microfabricated directly, which could then be used to create the final device.

Micromolding Techniques

Another method of fabricating tracts or channels utilizes micromold plating techniques. A photo-defined mold first is first produced, for example, by spin casting a thick layer, typically 150 $\mu$m, of an epoxy onto a substrate that has been coated with a thin sacrificial layer, typically about 10 to 50 nm. Arrays of cylindrical holes are then photolithographically defined through the epoxy layer, which typically is about 150 $\mu$m thick. (Despont, et al., "High-Aspect-Ratio, Ultrathick, Negative-Tone Near-UV Photoresist for MEMS," *Proc. of IEEE 10$^{th}$ Annual International Workshop on MEMS*, Nagoya, Japan, pp. 518–522 (Jan. 26–30, 1997)). The diameter of these cylindrical holes defines the outer diameter of the tracts. The upper surface of the substrate, the sacrificial layer, is then partially removed at the bottom of the cylindrical holes in the photoresist. The exact method chosen depends on the choice of substrate. For example, the process has been successfully performed on silicon and glass substrates (in which the upper surface is etched using isotropic wet or dry etching techniques) and copper-clad printed wiring board substrates. In the latter case, the copper laminate is selectively removed using wet etching. Then a seed layer, such as Ti/Cu/Ti (e.g., 30 nm/200 nm/30 nm), is conformally DC sputter-deposited onto the upper surface of the epoxy mold and onto the sidewalls of the cylindrical holes. The seed layer should be electrically isolated from the substrate. Subsequently, one or more electroplatable metals or alloys, such as Ni, NiFe, Au, Cu, or Ti, are electroplated onto the seed layer. The surrounding epoxy is then removed, leaving molds which each have an interior annular hole that extends through the base metal supporting the tracts. The rate and duration of electroplating is controlled in order to define the wall thickness and inner diameter of the tracts.

The molds made as described above and injection molding techniques can be applied to form the tracts or channels in the molds (Weber, et al., "Micromolding—a powerful tool for the large scale production of precise microstructures", Proc. SPIE—International Soc. Optical Engineer. 2879, 156–167 (1996); Schift, et al., "Fabrication of replicated high precision insert elements for micro-optical bench arrangements" Proc. SPIE—International Soc. Optical Engineer. 3513, 122–134 (1998). These micromolding techniques can provide relatively less expensive replication, i.e. lower cost of mass production.

Solid Free Form Manufacturing Techniques

As defined herein, SFF refers to any manufacturing technique that builds a complex three dimensional object as a series of two dimensional layers. The SFF methods can be adapted for use with a variety of polymeric, inorganic, and composite materials to create structures with defined compositions, strengths, and densities, using computer aided design (CAD).

Examples of SFF methods include stereo-lithography (SLA), selective laser sintering (SLS), ballistic particle manufacturing (BPM), fusion deposition modeling (FDM), and three dimensional printing (3DP). In a preferred embodiment, 3DP is used to precisely create channels and pores within a matrix to control subsequent cell growth and proliferation in the matrix of one or more cell types having a defined function, such as nerve cells.

The macrostructure and porous parameters can be manipulated by controlling printing parameters, the type of polymer and particle size, as well as the solvent and/or binder. Porosity of the matrix walls, as well as the matrix per se, can be manipulated using SFF methods, especially 3DP. Structural elements that maintain the integrity of the devices during erosion can also be incorporated. For example, to provide support, the walls of the device can be filled with resorbable inorganic material, which can further provide a source of mineral for the regenerating tissue. Most importantly, these features can be designed and tailored using computer assisted design (CAD) for individual patients to individualize the fit of the device.

Three Dimensional Printing (3DP).

3DP is described by Sachs, et al., "CAD-Casting: Direct Fabrication of Ceramic Shells and Cores by Three Dimensional Printing" *Manufacturing Review* 5(2), 117–126 (1992) and U.S. Pat. No. 5,204,055 to Sachs, et al., the teachings of which are incorporated herein. Suitable devices include both those with a continuous jet stream print head and a drop-on-demand stream print head. A high speed printer of the continuous type, for example, is the Dijit printer made and sold by Diconix, Inc., of Dayton, Ohio, which has a line printing bar containing approximately 1,500 jets which can deliver up to 60 million droplets per second in a continuous fashion and can print at speeds up to 900 feet per minute. Both raster and vector apparatuses can be used. A raster apparatus is where the printhead goes back and forth across the bed with the jet turning on and off. This can have problems when the material is likely to clog the jet upon settling. A vector apparatus is similar to an x-y printer. Although potentially slower, the vector printer may yield a more uniform finish.

3DP is used to create a solid object by ink-jet printing a binder into selected areas of sequentially deposited layers of powder. Each layer is created by spreading a thin layer of powder over the surface of a powder bed. The powder bed is supported by a piston which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three dimensional structure. The unbound powder supports temporarily unconnected portions of the component as the structure is built but is removed after completion of printing.

As shown in U.S. Pat. No. 5,204,055, the 3DP apparatus includes a powder dispersion head which is driven reciprocally in a shuttle motion along the length of the powder bed. A linear stepping motor assembly is used to move the powder distribution head and the binder deposition head. The powdered material is dispensed in a confined region as the dispensing head is moved in discrete steps along the mold length to form a relatively loose layer having a typical thickness of about 100 to 200 microns, for example. An ink-jet print head having a plurality of ink-jet dispensers is also driven by the stepping motor assembly in the same reciprocal manner so as to follow the motion of the powder head and to selectively produce jets of a liquid binder material at selected regions which represent the walls of each cavity, thereby causing the powdered material at such regions to become bonded. The binder jets are dispensed along a line of the printhead which is moved in substantially the same manner as the dispensing head. Typical binder droplet sizes are between about 15 to 50 microns in diameter. The powder/binder layer forming process is repeated so as to build up the device layer by layer. While the layers become hardened or at least partially hardened as each of the layers is laid down, once the desired final part configuration is achieved and the layering process is complete, in some applications it may be desirable that the form and its contents be heated or cured at a suitably selected temperature to further promote binding of the powder particles. In either case, whether or not further curing is required, the loose, unbonded powder particles are removed using a suitable technique, such as ultrasonic cleaning, to leave a finished device. Finer feature size is also achieved by printing polymer solutions rather than pure solvents.

Stereo-lithography (SLA) and selective laser sintering (SLS).

SFF methods are particularly useful for their ability to control composition and microstructure on a small scale for the construction of these medical devices. The SFF methods, in addition to 3DP, that can be utilized to some degree as described herein are stereo-lithography (SLA), selective laser sintering (SLS), ballistic particle manufacturing (BPM), and fusion deposition modeling (FDM).

Stereolithography is based on the use of a focused ultraviolet (UV) laser which is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired device is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biocompatible polymeric materials.

SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation of Austin, Tex.

Ballistic particle manufacturing (BPM) and Fusion deposition modeling (FDM)

BPM uses an ink-jet printing apparatus wherein an ink-jet stream of liquid polymer or polymer composite material is used to create three-dimensional objects under computer control, similar to the way an inkjet printer produces two-dimensional graphic printing. The device is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y.

FDM employs an x-y plotter with a z motion to position an extrudable filament formed of a polymeric material, rendered fluid by heat or the presence of a solvent. A suitable system is available from Stratasys, Incorporated of Minneapolis, Minn.

Polymer Materials, Binders and Solvents for use in SSF Techniques

Depending on the processing method, the material forming the matrix may be in solution, as in the case of SLA, or in particle form, as in the case of SLS, BPM, FDM, and 3DP. In the preferred embodiment, the material is a polymer. In SLS, the polymer must be photopolymerizable. In the other methods, the material is preferably in particulate form and is solidified by application of heat, solvent, or binder (adhesive). In the case of SLS and FDM, it is preferable to select polymers having relatively low melting points, to avoid exposing incorporated bioactive agent to elevated temperatures.

A number of materials are commonly used to form a matrix. Unless otherwise specified, the term "polymer" will be used to include any of the materials used to form the matrix, including polymers and monomers which can be polymerized or adhered to form an integral unit, as well as inorganic and organic materials, as discussed below. In a preferred embodiment the particles are formed of a polymer which can be dissolved in an organic solvent and solidified by removal of the solvent, such as a synthetic thermoplastic polymer, for example, ethylene vinyl acetate, poly (anhydrides), polyorthoesters, polymers of lactic acid and glycolic acid and other α hydroxy acids, polyhydroxyalkanoates, and polyphosphazenes, a protein polymer, for example, albumin or collagen, or a polysaccharide. The polymer can be non-biodegradable or biodegradable, typically via hydrolysis or enzymatic cleavage. Examples of non-polymeric materials which can be used to form a part of the device or matrix for drug delivery include organic and inorganic materials such as hydoxyapatite, calcium carbonate, buffering agents, and lactose, as well as other common excipients used in drugs, which are solidified by application of adhesive or binder rather than solvent. In the case of polymers for use in making devices for cell attachment and growth, polymers are selected based on the ability of the polymer to elicit the appropriate biological response from cells, for example, attachment, migration, proliferation and gene expression.

Photopolymerizable, biocompatible water-soluble polymers include polyethylene glycol tetraacrylate (Mw 18,500) which can be photopolymerized with an argon laser under biologically compatible conditions using an initiator such as triethanolamine, N-vinylpyrrolidone, and eosin Y. Similar photopolymerizable macromers having a poly(ethylene glycol) central block, extended with hydrolyzable oligomers such as oligo(d,1-lactic acid) or oligo(glycolic acid) and terminated with acrylate groups, may be used.

Examples of biocompatible polymers with low melting temperatures include polyethyleneglycol 400 (PEG) which melts at 4–8° C., PEG 600 which melts at 20–25° C., and PEG 1500 which melts at 44–48° C. Another low melting material is stearic acid, which melts at 70° C.

Other suitable polymers can be obtained by reference to The Polymer Handbook, 3rd edition (Wiley, N.Y., 1989), the teachings of which are incorporated herein.

A preferred material is a polyester in the polylactide/polyglycolide family. These polymers have received a great deal of attention in the drug delivery and tissue regeneration areas for a number of reasons. They have been in use for over 20 years in surgical sutures, are Food and Drug Administration (FDA)-approved and have a long and favorable clinical record. A wide range of physical properties and degradation times can be achieved by varying the monomer ratios in lactide/glycolide copolymers: poly-L-lactic acid (PLLA) and poly-glycolic acid (PGA) exhibit a high degree of crystallinity and degrade relatively slowly, while copolymers of PLLA and PGA, PLGAs, are amorphous and rapidly degraded.

Solvents and/or binder are used in the preferred method, 3DP, as well as SLA and BPM. The binder can be a solvent for the polymer and/or bioactive agent or an adhesive which binds the polymer particles. Solvents for most of the thermoplastic polymers are known, for example, methylene chloride or other organic solvents. Organic and aqueous solvents for the protein and polysaccharide polymers are also known, although an aqueous solution, for example, containing a crosslinking agent such as carbodiimide or glutaraldehyde, is preferred if denaturation of the protein is to be avoided. In some cases, however, binding is best achieved by denaturation of the protein.

The binder can be the same material as is used in conventional powder processing methods or may be designed to ultimately yield the same binder through chemical or physical changes that take place in the powder bed after printing, for example, as a result of heating, photopolymerization, or catalysis.

These methods and materials are further described in PCT/US96/09344 *"Vascularized Tissue Regeneration Matrices Formed by Solid Free-Form Fabrication Meth-* ods" Massachusetts Institute of Technology and Children's Medical Center Corporation.

2. Fibrous Scaffolds for Implantation

Fibrous scaffolding can be used to implant the cells, for example, as described in U.S. Pat. No. 5,759,830 to Vacanti, et al. The design and construction of the scaffolding is of primary importance. The matrix should be a pliable, non-toxic, porous template for vascular ingrowth. The pores should allow vascular ingrowth and the injection of cells into the scaffold without damage to the cells or patient. The scaffolds are generally characterized by interstitial spacing or interconnected pores in the range of at least between approximately 100 and 300 microns in diameter. The matrix should be shaped to maximize surface area, to allow adequate diffusion of nutrients and growth factors to the cells and to allow the ingrowth of new blood vessels and connective tissue.

The same type of polymers can be used as in the Solid Free Form Manufacturing techniques described above. In the preferred embodiment, the matrix is formed of a bioabsorbable, or biodegradable, synthetic polymer such as a polyanhydride, polyorthoester, polyhydroxy acid such as polylactic acid, polyglycolic acid, or a natural polymer like polyalkanoates such as polyhydroxybutyrate and copolymers or blends thereof. Proteins such as collagen can be used, but is not as controllable and is not preferred. These materials are all commercially available. Non-biodegradable polymers, including polymethacrylate and silicon polymers, can be used, depending on the ultimate disposition of the growing cells.

In some embodiments, attachment of the cells to the polymer is enhanced by coating the polymers with compounds such as basement membrane components, agar, agarose, gelatin, gum arabic, collagens types I, II, III, IV, and V, fibronectin, laminin, glycosaminoglycans, mixtures thereof, and other materials, especially attachment peptides and polymers having attachment peptides or other cell surface ligands bound thereto, known to those skilled in the art of cell culture. Vitrogen—100 collagen (PCO 701) has been used in these experiments.

3. Hydrogel Matrices for Implantation

Polymeric materials which are capable of forming a hydrogel can be utilized. The polymer is mixed with cells for implantation into the body and is permitted to crosslink to form a hydrogel matrix containing the cells either before or after implantation in the body. In one embodiment, the polymer forms a hydrogel within the body upon contact with a crosslinking agent. A hydrogel is defined as a substance formed when an organic polymer (natural or synthetic) is crosslinked via covalent, ionic, or hydrogen bonds to create a three-dimensional open-lattice structure which entraps water molecules to form a gel. Naturally occurring and synthetic hydrogel forming polymers, polymer mixtures and copolymers may be utilized as hydrogel precursors. See for example, U.S. Pat. No. 5,709,854 and WO 94/25080 by Reprogenesis.

In one embodiment, calcium alginate and certain other polymers that can form ionic hydrogels which are malleable. For example, a hydrogel can be produced by cross-linking the anionic salt of alginic acid, a carbohydrate polymer isolated from seaweed, with calcium cations, whose strength increases with either increasing concentrations of calcium ions or alginate. The alginate solution is mixed with the cells to be implanted to form an alginate suspension which is injected directly into a patient prior to hardening of the suspension. The suspension then hardens over a short period of time due to the presence in vivo of physiological concentrations of calcium ions. Modified alginate derivatives, for example, more rapidly degradable or which are derivatized with hydrophobic, water-labile chains, e.g., oligomers of $\epsilon$-caprolactone, may be synthesized which have an improved ability to form hydrogels. Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Additional examples of materials which can be used to form a hydrogel include polyphosphazines and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin (although this is not preferred since thrombin may stimulate tumor growth via a pathway that MIS may have to overcome, such as EGF-stimulated proliferation), polymers such as polyvinylpyrrolidone, hyaluronic acid and collagen. Polymers such as polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives are particularly useful. Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669. Additionally, water soluble polymers which include cinnamoyl groups which may be photochemically crosslinked may be utilized, as disclosed in Matsuda et al.,*ASAID Trans.*, 38:154–157 (1992).

II. Methods for Engineering and Implantation of Cells

A. Disorders to be Treated

A variety of conditions that produce abnormal growth, including treatment of malignant and benign neoplasias, vascular malformations (hemangiomas), inflammatory conditions including those resulting from infection, especially chronic or recalcitrant conditions such as those in the sinuses or which are cystic, keloid formation, endometriosis, congenital or endocrine abnormalities such as testotoxicosis (Teixeira et al, PNAS 1999) and other conditions that produce abnormal growth, can be treated.

Examples of tumor cells that can be treated with MIS include primary and metastatic growth of the following: ovarian adenocarcinomas, endometrial adenocarcinomas, cervical carcinomas, vulvar epidermoid carcinomas, ocular melanomas, prostate, breast, and germ cell tumors. As initially demonstrated with MIS transfected cells, this methodology can be used for delivery of a large number of proteins to control abnormal tissue growth, particularly other members of the TGFP family. Coupled with minimally invasive delivery systems, the biodegradable implants producing the therapeutic proteins from transfected autologous cells can be introduced into a variety of sites to deliver therapeutics, particularly where a local effect is advantageous. This allows use of a variety of recombinant proteins without the need for complex purification protocols.

B. Engineering of Cells

In the preferred embodiment, patient cells are transfected with the gene to be expressed, for example, rhMIS cDNA, to produce cells having stably incorporated therein the DNA encoding the molecules to be expressed. Methods yielding transient expression, such as most adenoviral vectors, are not preferred. Stable transfectants are obtained by culturing and selection for expression of the encoded molecule(s). Those cells that exhibit stable expression are seeded onto/into the appropriate matrix and then implanted using techniques such as those described in the following examples.

C. Seeding of Matrices

The level of expression of the bioactive molecules is measured prior to implantation to insure that an adequate number of cells is implanted. In general, the higher the number of cells implanted, the better. Cells are preferably cultured initially in vitro, then implanted before the matrix degrades but when the level of bioactive molecules is highest. An example of a suitable seeding density is between 1 and $10 \times 10^6$ cells on a matrix with a surface area of 0.25 $cm^2$.

D. Implantation of Matrices

The devices are implanted into the patient at the site in need of treatment using standard surgical techniques. In one embodiment, the device is constructed, seeded with cells, and cultured in vitro prior to implantation. The cells are cultured in the device, tested for high MIS production by ELISA, then implanted.

The technique described herein can be used for delivery of many different cell types for different purposes. Other endocrine producing transfectant cells can also be implanted. The matrix may be implanted in one or more different areas of the body to suit a particular application. Matrices with hepatocytes or other high oxygen organ cells may be implanted into the mesentery to insure a good blood supply. Sites other than the mesentery for injection or implantation of cells include the ovarian pedicle, subcutaneous tissue, retroperitoneum, properitoneal space, and intramuscular space. The use of ovarian pedicle for MIS producing implants cause ovary and fallopian tubes to adhere to implants (Kristjansen, et al., 1994).

The need for these additional procedures depends on the particular clinical situation.

III. EXAMPLES

The present invention will be further understood by reference to the following non-limiting examples.

Example 1

Production of MIS in CHO Cells In Vitro

Materials and Methods

Polyglycolic acid fibers (approximately 12 microns diameter) obtained from Albany International were cut into 0.5×0.5 cm squares. $1 \times 10$ $10^6$ CHO B9 cells are seeded onto the mesh by the static seeding method. After 4 hours, the mesh was transferred into a new dish containing 10 ml of fresh media. Media MIS concentration was measured serially over seven days by ELISA. Another CHO cell line, CHO L9, which is transfected with a mutated rhMIS gene that produces non-cleavable bioinactive protein, was placed on the mesh as a negative control for the implant experiments. Samples were also placed in the organ culture assay to determine MIS bioactivity.

Results

In preliminary in vitro experiments, CHO B9 cells seeded onto a polyglycolic acid matrix produced large (i.e. microgram) quantities of bioactive MIS as determined by ELISA (Hudson et al., J Clin Endocrinol Metab. 70: 16–22, 1990) and by a standard organ culture bioassay (Donahoe et al., 1977) which detects regression of the Müllerian duct. The results are shown in FIG. 1. After eight days, more than 2000 ng MIS were produced.

Example 2

Regression of Tumors by MIS-producing Cells Seeded onto Polymeric Matrices Implanted into Animals As described in Example 1, in vitro CHO cells transfected with the human MIS gene were seeded onto a polyglycolic acid matrix and produced large quantities (micrograms) of bioactive MIS as determined by ELISA and by a standard in vitro organ culture bioassay. A production rate of 400 ng/day/device was determined, corresponding to a production rate per cell of 3 pg/cell/day. By serial sampling it was determined that 7–8 days incubation produced optimal bioactive MIS production by the mesh impregnated with the B9 clone (a cell line tranfected with the human MIS genomic sequence).

Studies were then undertaken to determine MIS production with this model in vivo. The MIS producing matrices were implanted into the ovarian pedicle of B and T cell deficient 6-week-old female SCID mice. Serum levels of MIS were measured to determine the rate of rise and duration of MIS production by the explants. Supraphysiologic levels of MIS were detected in mouse sera within three days of implantation. It was determined that the amount of MIS produced depends on the size of the mesh implanted.

Several ovarian cancer cell lines were tested in vitro for inhibition by MIS. Human ovarian cancer cell lines (IGROV-1, OVCAR-8, OVCAR-5) were plated on soft agarose and colony counts were determined as an assay end point. Significant inhibition (20–80%) of these ovarian cancer cell lines by MIS was observed. Ovarian cancer cell lines that were responsive to MIS in vitro were then placed beneath the renal capsules of SCID mice. These tumors grew two to four fold at two weeks after implantation with IGROV-1 showing the best growth. This represents an animal model of tumor growth.

The inhibitory properties of the MIS produced on the mesh was then tested in vivo against the IGROV-1 tumor cell line. B9 and L9 impregnated meshes were implanted in mice. The L9 cells produce bio-inactive MIS and served as the negative control for the experiment. MIS produced by the B9 clones significantly inhibited the growth of the human ovarian cancer cell line in vivo, as follows.

Materials and Methods

Animals

Severe combined immunodeficient (SCID) female mice and athymic nude mice (6 weeks old, average weight 18–20 g) were obtained from and studied in the Edwin L. Steele Laboratory, Massachusetts General Hospital, Boston, Mass. All animals were cared for and experiments performed in this facility under AAALAS approved guidelines using protocols approved by the Institutional Review Board-Institutional Animal Care and Use Committee of the Massachusetts General Hospital protocol #98–4254).

Cells

The IGROV-1 human ovarian cancer cell line was obtained from the American Type Cell Culture and maintained in Dulbecco's Modification of Eagle's Medium (DMEM) supplemented with glutamine, penicillin, streptomycin, and 10% MIS-free female fetal calf serum. The cells were grown at 37° C. in a humidified chamber perfused with 5% $CO_2$ in air. At 80% confluency the cells were passed at a ratio of 1:4 and were carried for up to twelve passages.

The CHO-B9 cell line was formed by cloning the human MIS gene into dihydrofolate reductase deficient Chinese hamster ovary cells as described previously (Cate, et al. Cell, 45: 685–698 (1986)). Alternatively, a mutated cDNA which produces a bioinactive form of human MIS was also cloned into the CHO cells, resulting in the CHO-L9 cell line (Kurian et al, Clin. Cancer Res. 1(3):343–349 (1995). Both cell lines were maintained in DMEM supplemented with glutamine, penicillin, streptomycin, methotrexate, and 5% MIS-free female fetal calf serum.

Subrenal Capsule Assay

Following the method of Bogden et al. Exp Cell Biol 47(4):281–93 (1979), as modified by Fingert, et al. Cancer Res., 47: 3824–3829 (1987), the IGROV-1 tumor cell line was tested for growth in vivo in a murine subrenal capsule assay (Donahoe et al, 1984). Ten million cells were centrifuged at 1500 rpm for 5 min to form a pellet. 300 micrograms of fibrinogen (Sigma; 20 mg/ml, dissolved in phosphate-buffered saline, pH 7.4) were added to the pellet, followed by 0.16 units of thrombin (Sigma; 20 unit/ml, dissolved in double-strength DMEM). This mixture was incubated at 37° C. for 15 minutes. The cell clot thus formed was then cut into approximately 50 fragments (10 microliter volume, 200,000 cells each) in preparation for implantation. Selected fragments were dissolved with trypsin and cells counted to confirm uniformity of cell number.

After inducing anesthesia using ketamine/xylazine (100/10 mg/kg BW, i.m.) a subcapsular space was developed in the left kidney with a 19-gauge needle trocar and a cell clot measuring approximately 1×1 ocular micrometer units at 7×magnification was introduced. The longest diameter (L1) of the implant and the diameter perpendicular to the longest diameter (W1) were measured with the ocular micrometer of a dissecting microscope. The graft volume was estimated as L1×W1×W1. The implant was allowed to grow for 2–3 weeks at which time similar measurements were obtained at the same focal distance as the initial measurement to calculate the graft size ratio ([L2×W2×W2]/[L1×W1×W1]). Histology of the tumors was reviewed to verify that the implants were viable and lacked both an inflammatory infiltrate and central necrosis. The growth of the tumor was measured at weekly intervals and the time of the experiment chosen so that 3 to 4×growth was achieved for the control-treated tumors.

Preparation of the Polymer-cell Graft and its in vitro Production of MIS

Biodegradable polymer consisting of 1 millimeter thick sheets of nonwoven fibers of polyglycolic acid (density 70 mg/cc, fiber diameter 14 $\mu$m, and average pore size 250 $\mu$m) was obtained from Smith and Nephew (York County, UK). The sheets were sectioned into 0.5 cm² squares which were placed in a 12-well tissue culture plate (Costar, Cambridge, Mass.), sterilized with 95% ethanol, and washed with phosphate buffer saline (PBS). Sterile filtered IN sodium hydroxide was added to each well for 60 seconds to make the polymer hydrophilic and the polymer was washed with distilled water and coated with collagen (Vitrogen 3 mg/ml diluted 100× in sterile PBS) added to the wells for one hour at room temperature. The treated polymer squares were further washed with sterile PBS. Transfected CHO cells were remove from culture flasks with trypsin-EDTA (Gibco) and resuspended in DMEM supplemental with 10% female fetal calf serum. After counting the cells in a Coulter counter, 1–2×10⁶ suspended cells were seeded with a micropipet onto each polymer square and absorbed onto the interstices of the polymer matrix during a subsequent incubation of 1–2 hours at 37° C. in 5% $CO_2$ air to allow sufficient time for attachment, after which time fresh media was added and the wells returned to the incubator for attachment, after which time fresh media was added and the wells returned to the incubator for three to seven days. Growth media was changed every other day. The concentration of MIS in the media was measured serially using a sensitive MIS ELISA (Hudson et al, 1990) and an MIS specific organ culture assay (Donahoe 1977) was used to assess MIS bioactivity on selected samples.

Implantation of polymer-cell graft and the IGROV-1 tumor cell line into SCID mice On day 0 the cells are seeded onto the polymer. 3–7 days later, when the media MIS levels reach 200 ng/ml, the polymer-cell graft is implanted into the right ovarian pedicle of SCID mice. On day 10–14, the IGROV-1 tumor in the form of a cell clot is implanted under the left renal capsule of the mice. 2–3 weeks after implantation, the size of the tumors is measured. The left kidney and the right ovarian pedicle are removed for immunohistochemical and/or histologic analysis. Serum is collected throughout the protocol to determine MIS concentrations.

Three to seven days after seeding with CHO-B9 or CHO-L9 cells, when serum MIS was above physiologic levels, a 5×5×1 mm polymer square was implanted into the right ovarian pedicle of SCID mice as described for tumor samples by Kristjansen, et al. Microvasc. Res., 389–402 (1994). After induction of anesthesia with ketamine/xylazine, a one centimeter horizontal incision was made in the right flank. The ovarian pedicle was identified, delivered out of the wound, and the polymer-cell graft laid on the ovarian pedicle and sutured in place with 6-0 prolene. Six to thirteen days later, the levels of circulating MIS were determined. When they approached supraphysiologic levels, the IGROV-1 tumor cell line was prepared in a fibrin/thrombin cell clot and implanted under the left renal capsule as described above. Different sized polymers (0.125, 0.25, 0.5, and 1.0 cm²) seeded with CHO-B9 cells were implanted into SCID mice and serum MIS levels measured to determine the optimal size of the polymer implant. Two to three weeks after implantation of the IGROV-1 cell clot, the left kidney was exposed and the dimensions of the implanted tumor measured. The graft size ratio was calculated and comparisons made between groups of animals receiving the B9, L9, or empty polymer. Also, at this time, the right ovarian pedicle (location of polymer implantation) was removed and measured, and selected implants examined by immunohistochemistry or routine histology. The animals implanted with CHO-B9 seeded polymer served as the experimental group and the animals implanted with CHO-L9 seeded or empty polymer served as controls.

Serum MIS levels and bioassay

MIS was measured at various time points after polymer implantation using a human MIS-specific ELISA described previously (Hudson et al, 1990). MIS-containing serum was placed in the MIS organ culture assay (Donahoe et al, 1977) to correlate bioactivity of the MIS present in the sample to the MIS levels as measured by ELISA.

Tissue Analysis

The tissue formed from the cell-polymer implant in the right ovarian pedicle and the kidneys with implanted IGOV-1 cell clot were fixed in 5% picric acid and 15% formalin in PBS. The tissue was then processed and cut into 8 micron sections prior to staining either for routine histologic analysis or for immunohistochemistry (Gustafson et al, N.Eng.J.Med. 326(7):466–471(1992). Viability of the tumors was confirmed as they were evaluated for central necrosis or an inflammatory infiltrate. Selected ovarian pedicles were harvested earlier during the course of the experiment and examined histologically to determine the rate of biodegradation of the polymer.

Statistics

Values for the tumor graft-size ratio are expressed as mean +/− standard error (SE). An unpaired t-test performed by 'STATVIEW' and analysis of variance (AVOVA) performed by 'EXCEL' were used to determine the level of statistical significance (p values).

Results

Production of MIS in vivo

Figure 2A:
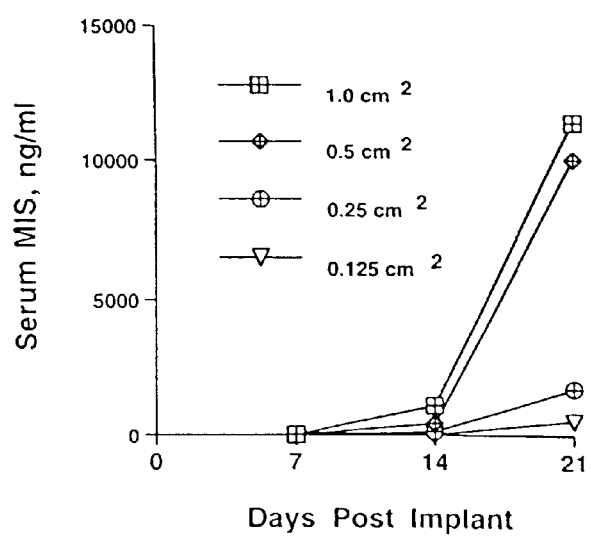
FIGS. 2A–C are graphs of MIS production on polymeric implants in mice.

The polymer-cell graft was incubated in vitro for three to seven days, at which time MIS levels of 100–400 ng/ml were measured in the media and the graft was implanted into the ovarian pedicle of mice. Serum MIS was measured by ELISA in the animals implanted with the different sized polymer squares (FIG. 2A). MIS levels in the animals implanted with polymer squares measuring 1.0 (n=4) and 0.5 (n=4) $cm^2$ were supraphysiologic at two weeks following implanation and exceeded 1 microgram/ml 3 weeks after implantation. In the animals with smaller squares measuring 0.25 (n=4) and 0.125 (n=4) $cm^2$ the MIS levels were supraphysiologic by three weeks following implantation. 0.5 cm2 was selected as the optimal size of seeded graft for implantation. The CHO cell line would not grow in animals made immunosuppressed by inactivation of the RAG-2 gene, hence the SCID mouse where growth and MIS production were robust was selected.

Figure 2B:
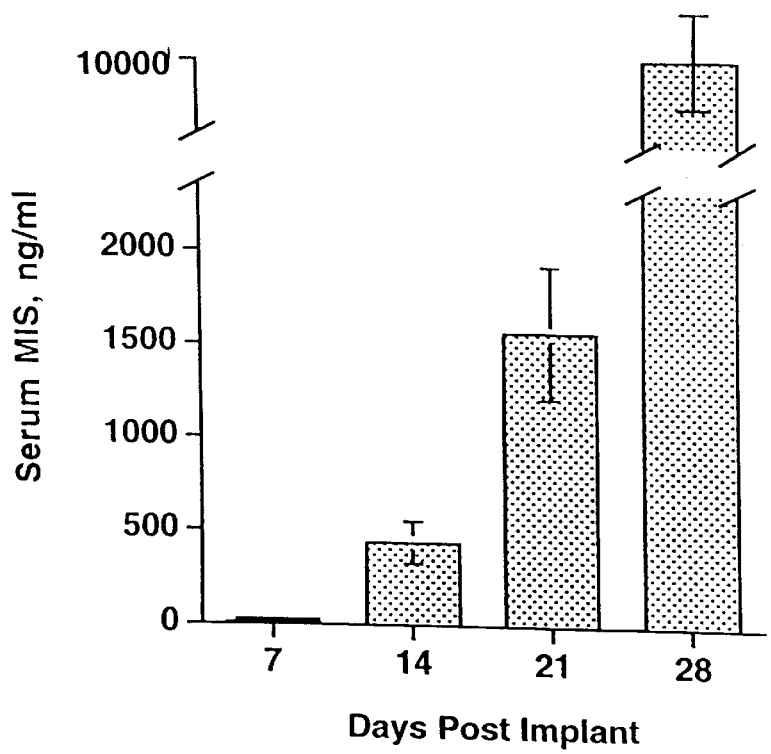
Figure 2C:
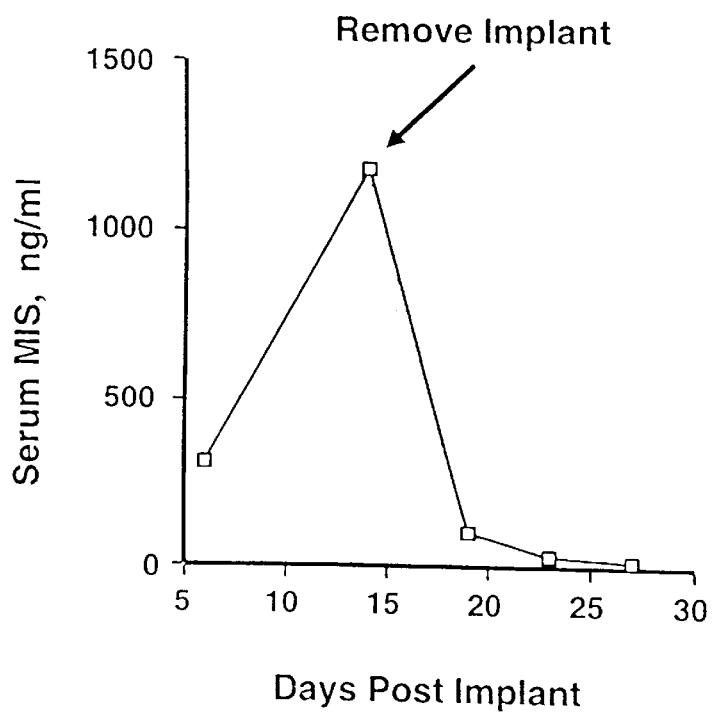

Serum MIS was measured by ELISA at 7, 14, 21, and 28 days after-implanatation of a polymercell graft measuring 0.5 $cm^2$ (n=40). At 14 days, the levels of MIS measured 100–500 ng/ml and at 28 days the levels measured 7–10 micrograms/ml (FIG. 2B). When the polymer-cell implant was removed, the serum levels were undetectable within 7 days (n=1) (FIG. 2C).

Sera from mice with high MIS levels were analyzed in the MIS bioassay to determine the bioactivity of the MIS produced by the polymer-cell implant. The samples produced complete regression of the Mullerian duct in the organ culture assay, indicating that the MIS in the serum of animals retained bioactivity. The MIS produced in vivo is bioactive. When placed in an organ culture assay, serum from the animals with a CHO-B9 polymer-cell graft implant causes complete regression of the rat Mullerian duct, leaving only the Wolffian duct. The negative control culture shows both Mullerian and Wolffian ducts.

After two weeks in vivo, the polymer-cell graft formed a firm, living mass of tissue throughout the polymer fibers, which began resorbing. After 4 weeks in vivo, the biodegradable polymer could no longer be detected and the polymer-cell graft grew into a rounded, well-contained mass with an approximate diameter of 1.0 cm. There was no evidence of spread of CHO-B9 cells beyond the mass formed in the ovarian pedicle during the duration of the experiment. The mass consisted histologically of epithelial cells with evidence of ingrowth of blood vessels from the ovarian pedicle. Immunohistochemical analysis confirmed the cells growing on the polymer continued to synthesize MIS. Immunohistochemistry of the polymer-cell graft after 4 weeks in vivo indicates ongoing production of MIS by the implanted cells. The polymer-cell graft stained with an antibody to human MIS is in marked contrast to the staining pattern seen using a control antibody.

Inhibition of tumor growth by MIS produced by polymer-cell implant

The IGROV-1 tumor cell line, when implanted into the subrenal capsule of the SCID mice, formed measurable tumors growing to reach a volume graft-size ratio of 3–4 three weeks after implantation. Histologic analysis of these tumors demonstrated well-formed growths with neovascularization from the underlying kidney parenchyma. There was minimal necrosis and inflammatory infiltrate. After 3 weeks of exposure to MIS, the tumor is approximately one third the size of the control and also has minimal necrosis or inflammation. When the IGROV-1 tumor cell line was implanted under the renal capsule of nude athymic mice, the tumors failed to achieve 3–4 fold growth three weeks after implantation. Hence the SCID mice were selected for use in subsequent experiments.

Figure 3A:
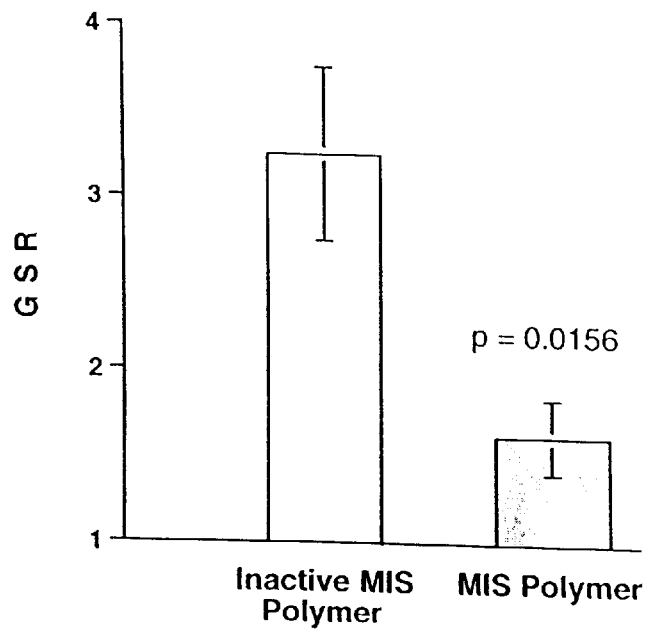
FIGS. 3A and 3B are graphs of MIS inhibition of the human ovarian tumor cell line IGROV-1 tumor growth in animals implanted with CHO B9 cells seeded on polyglycolic acid mesh as a function of graft size ratio (mean ± SEM), compared to a mesh seeded with non-transfected L9 cells as a negative control. The graft-size ratio represents the size of the tumor at two weeks divided by the starting size of the tumor and represents a measure of tumor growth. The L9 animals are represented by the squares and the B9 animals by the diamonds. The dashed line indicates the mean ± the standard error.

Animals implanted with the bioactive MIS-producing CHO-B9 polymer (n=8) showed very little net growth of the IGROV-1 implant, achieving a mean graft-size ratio +/− the standard error of the mean of 1.62+/−0.218 (FIG. 3A). The tumors implanted into the bioinactive MIS-producing CHO-L9 polymer (n=10) achieved a mean gift-size ratio of 3.25+/−0.506. This difference was statistically significant with a p-value of 0.016 (FIG. 3A).

Figure 3B:
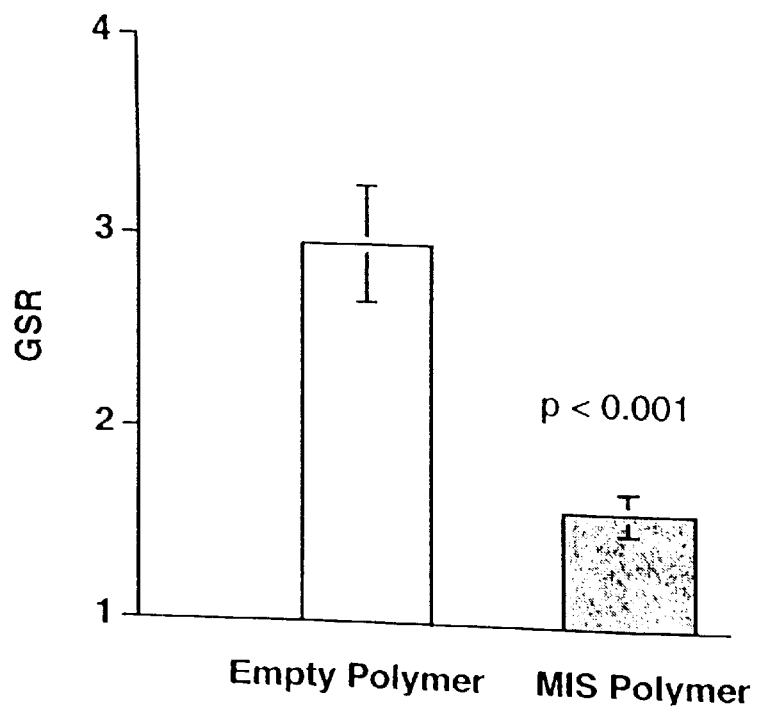

Three experiments were performed in which animals were implanted with the bioactive MIS-producing CHO-B9 polymer or polymer without cells. In the first experiment the graft-size-ratios of IGROV-1 tumors were 1.323+/−0.168 (n=10) for the animals with CHO-B9 polymer and 3.427+/= 0.682 (n=10) for the animals with polymer alone. In the second experiment the graft-size-ratio of the tumors in animals implanted with CHO-B9 polymer and polymer alone were 2.025+/−0.198 (n=10) and 3.024+/−0.454 (n=10). In the third experiment the graft-size-ratio of the tumors in animals implanted with CHO-B9 polymer and polymer alone were 1.427+/−0.147 (n=10) and 2.447+/−0.375 (n=10). The average graft-size ratios for all three experiments combined were 1.592+/−0.112 in the CHO-B9 polymer animals and 2.966+/−0.299 in the animals with empty polymer (FIG. 3B). The difference in graft-size-ratio between the two groups was statistically significant with a p-value <0.001.

In summary, cells in this study were transfected with the gene encodinig human MIS, seeded onto biodegradable polyglycolic acid fibers, and shown to produce biologically active MIS in vitro. When the polymer-cell grafts were implanted into animals, the continually produced MIS could be detected in the serum of the animals within one week of implantation (FIGS. 2A, B). Over time, secreted MIS was detected by ELISA in increasing concentrations, and the serum, when tested in the standard MIS in vitro bioassay, was biologically active (FIGS. 3A,B). There were no adverse effects in the animals as a result of the either the presence of the polymer, the growing cells, or the high levels on MIS. Removal of the polymer-cell graft resulted in declining and, after one week, undetectable levels of MIS (FIG. 2C) suggesting no spread of cells from the ovarian pedicle. When tumor cell line responsive to MIS in vitro was implanted in the subrenal capsule of the mice containing the MIS secreting graft, the growth of the target tumor was slowed considerably. The graft-size ratio of the measured tumors was significantly smaller compared to the growth of tumors implanted in animals with a polymer secreting biologically inactive MIS or a polymer secreting no MIS (FIGS. 3A, 3B). Thus only bioactive MIS and not a CHO cell product or biopolymer component was responsible for the growth inhibition. Histologic analysis confirmed the three-dimensional growth of the tumors and demonstrated lack of necrosis or excess inflammation that could alter the size of the controls.

Example 3 rhMIS Production by Genetically Engineered, Autologous Fibroblasts

To be used clinically, MIS must be administered to patients in a safe and cost effective manner in sufficient quantities to achieve tumor inhibition. MIS is a molecule that is produced by the Sertoli cells of the testis in the male and the granulosa cells of the ovary in the female. It serves the known function of Mullerian duct regression in the developing male fetus and likely serves as a modifier of cell growth and differentiation in the male and female throughout life. MIS is a complex molecule consisting of 70 kDa homodimer subunits that requires protease mediated cleavage for biological activity; therefore, production and delivery of purified MIS is predicted to be a complicated and costly endeavor. As an alternative to production of the purified protein, the use of biodegradable polymer seeded with MIS-producing transfected cells can deliver biologically active MIS in quantities sufficient to achieve serum levels above the highest measured in newborn males, while avoiding complicated purification protocols.

The studies described herein demonstrate proof of principle for the device using a partially transformed Chinese hamster ovary epithelial cell line that can be tumorigenic in immunosuppressed mice. Normal human fibroblast cell lines and mouse fibroblasts harvested from the peritoneum of animals with rhMIS constructs have now been transfected. Wild type and more easily cleavable MIS (S428R, Kurian et al., 1995) constructs will be transfected into fibroblasts using state of the art stable transfection techniques optimized for transfection efficiency and MIS production followed by clonal selection of the cells that produce the greatest concentration of MIS. These will be seeded onto the biodegradable mesh and implanted into mice and experiments will be repeated as with the CHO B9 cells. These experiments will be used to establish the optimal geometry of the mesh that will produce the highest concentration of MIS.

Human lung fibroblast cell lines IMR-90 will be permanently transfected with two monocistronic constructs encoding hygromycin resistance and one of either pCDNA-vector or pCDNA-K2, a CMV-driven MIS ligand expression construct. Transfection will be performed using either Fugene 6 transfection reagent (Boehringer Mannheim) or using the standard calcium phosphate DNA precipitation technique. Cells will be plated in 100 cm$^2$ well plates. When they reach 60 to 80% of confluence, Fugene 6 at 2 µg/ml will be added for 48 hours and washed. IMR-90 human fibroblast cells have been transfected using the Fugene system with 0.5 µg hygromycin and 5 µg of the K2 constructs, as well as vector alone, and these are now being selected in high concentration hygromycin media (750 µg/ml of hygromycin, Boehringer Mannheim). After two weeks the media will be tested for MIS production by ELISA. Clones will be replated at 10 cells/well in 24 well plates and expanded in media containing 100 µg/ml of hygromycin. Clones will be selected for MIS production by ELISA of overlying media; high producers will be grown on biodegradable matrices and implanted in SCID mice harboring ovarian tumors. Primary human fibroblasts originally taken from patients to study expression of androgen receptor will be similarly tested for transfection efficiency using retroviral transfection and then clonally selected for maximum production of MIS.

Since primary fibroblasts are difficult to transfect, an adenovirus transfection system adapted from one that used to transfect primary Sertoli cells will be used. Briefly, 32.5 µl of adenovirus, diluted in PBS with 10% glycerol and 0.2% BSA, is added to the fresh medium and incubated for 1 hour at 37 C. After 1 hour of incubation, cells will be washed with HBSS and added in 500 µl of fresh medium. 48 hours later cells the media will be collected and assayed for MIS using the MIS ELISA and the organ culture assay for regression of the Mullerian Duct. The IMR-90 cells in 24 well plates have been transfected with a CMV-GFP virus and detected near 100% infection by fluorescence. Three other human fibroblast lines followed by primary fibroblasts will be transfected, then virus to express the MIS construct generated.

Since growth after transfection and cloning may be inefficient in fibroblast cell lines and primary fibroblasts, clones of cells may have to be screened before choosing the best MIS producers to seed the mesh. An alternative approach is to grow pools of cells ex vivo on individual biodegradable meshes and then to test and select each mesh for maximal production of MIS prior to implantation in vivo for serial measurements of MIS in each animal's serum. Once the method of "cloning" in the mesh or in monolayer culture is established, and the highest ex vivo producers are selected, the loaded meshes will be implanted in an ovarian fat pad and levels of MIS production measured and compared to the levels produced by CHOB9 cell impregnated implants or by MIS containing Alzet pumps.

The next step is to implant tumors in the subrenal capsule of 20 SCID mice for as many days as it takes for the tumor to reach 4 times the original implant volume measured at length×width×width at the time of implantation (Parry et al., 1992). The time to reach 4× for each cell line and the time to reach maximum production per unit number of cells and unit size of mesh will be determined, then after the mesh is producing high levels of MIS the tumors will be implanted. Growth between mesh containing MIS and non MIS producing fibroblasts (n=20) and Alzet delivered MIS positive controls (n=20) will then be compared. Subsequently tumor growth will be allowed to reach 3–4× in size. Then MIS producing versus non-producing fibroblast-containing mesh will be implanted intraperitoneally and growth of tumors compared between groups to see if MIS prevents growth and/or reverses growth of the tumor implants.

The biodegradable mesh impregnated with autologous fibroblasts will then be implanted into patients. It is important to note that either dermal fibroblasts, peripheral or marrow stem cells, or peritoneal mesothelium will be requested from patients. The autologous cells will then be transfected and cloned and the optimal MIS producing fibroblasts will be impregnated in the biodegradable matrix plugs. The matrices will then be implanted into the ovarian pedical in the peritoneal cavity of the ovarian cancer patient from whom the fibroblasts were taken. This may entail implantation in or near the tumors intraperitoneally for the ovarian cancer model or in the liver, brain, heart, blood vessels, joints, or other organs, as the protein of interest or therapeutic indication dictates.

This ongoing work uses transfected fibroblasts which grow robustly on the polymer. To avoid immunosuppression in patients, a sample of the patient's own cells will be transfected with the human MIS gene sequence. The cells could be fibroblasts or myofibroblasts obtained from a small skin or muscle biopsy or stem cells from peripheral blood or bone marrow. The cells would be grown on biodegradable polymer in vitro and implanted in the patient, providing continual production of MIS to serve as an inhibitor of tumor growth.

Modifications and variations of the present invention are intended to come within the scope of the following claims.

We claim:

1. A method for treating abnormal cell or tissue growth that is treatable with MIS, in a subject in need thereof, comprising implanting in the subject a cell-matrix structure, wherein the cell-matrix structure comprises a matrix having attached thereto allogeneic or autologous cells that have been genetically engineered to stably express MIS in an amount sufficient to treat the abnormal cell or tissue growth, and wherein the abnormal cell or tissue growth is vulvar epidermoid carcinoma, cervical carcinoma, endometrial adenocarcinoma, ovarian adenocarcinoma, or a breast tumor.

2. The method of claim 1 wherein the abnormal cell or tissue growth is.

3. The method of claim 1 wherein the matrix is selected from the group consisting of fibrous scaffolds, polymeric hydrogels, and micromachine or micromolded substrates.

4. The method of claim 1 wherein the cells that have been genetically engineered are of a different cell type than the abnormal cell or tissue.

5. The method of claim 1 wherein the abnormal cell or tissue growth is ovarian adenocarcinoma.

6. The method of claim 1 wherein the abnormal cell or tissue growth is malignant.

7. The method of claim 1 wherein the tissue is ovarian tissue.

8. The method of claim 1 wherein the matrix comprises a biodegradable polymer of polyglycolic acid.

* * * * *

UNITED STATES PATENT AND TRADEMARK OFFICE
CERTIFICATE OF CORRECTION

PATENT NO. : 6,692,738 B2
DATED : February 17, 2004
INVENTOR(S) : MacLaughlin et al.

It is certified that error appears in the above-identified patent and that said Letters Patent is hereby corrected as shown below:

<u>Title page,</u>
Item [74], *Attorney, Agent or Firm,* please change "Lesby" to -- Leahy --.

<u>Column 24,</u>
Line 2, after "is" please add -- benign --.

Signed and Sealed this

First Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,692,738 B2  Page 1 of 1
APPLICATION NO. : 09/770339
DATED : February 17, 2004
INVENTOR(S) : Joseph P. Vacanti et al.

It is certified that error appears in the above-identified patent and that said Letters Patent is hereby corrected as shown below:

At page 6, column 1, line 7, delete

"The United States government has certain rights in this invention by virtue of Grant No. CA17393 from the National Institutes of Health to Patricia K. Donahoe and David T. MacLaughlin; National Institute of Health grant No. CA71345; and Department of Defense 1200-202487 to Joseph P. Vacanti."

and insert

--This invention was made with Government support under Grant Nos. CA071345 and CA017393 awarded by the National Institutes of Health and Grant No. DAMD17-99-2-9001 awarded by the U.S. Department of the Army. The Government has certain rights in this invention.--

Signed and Sealed this

Twenty-second Day of June, 2010

David J. Kappos
*Director of the United States Patent and Trademark Office*